(12) United States Patent
Jimenez Cerrato et al.

(10) Patent No.: US 6,464,635 B1
(45) Date of Patent: Oct. 15, 2002

(54) DIAPER WITH INDICATORS SENSITIVE TO THE STATUS OF THE IMPREGNATED URINE AND VISIBLE FORM OUTSIDE

(76) Inventors: Paula Jimenez Cerrato, Avenida Amilcar Barca, 17-4°, E-11008 Cadiz (ES); Munuel Chamero Martinez, Avenida Amilcar Barca, 17-4°, E-11008 Cadiz (ES)

( * ) Notice: Subject to any disclaimer, the term of this patent is extended or adjusted under 35 U.S.C. 154(b) by 0 days.

(21) Appl. No.: 09/554,773

(22) PCT Filed: Sep. 16, 1999

(86) PCT No.: PCT/ES99/00291

§ 371 (c)(1),
(2), (4) Date: Jun. 14, 2000

(87) PCT Pub. No.: WO00/15169

PCT Pub. Date: Mar. 23, 2000

(30) Foreign Application Priority Data

Sep. 16, 1998 (ES) .............................................. 9801948

(51) Int. Cl.[7] .................................................. A61B 5/00
(52) U.S. Cl. ........................ 600/362; 604/361; 604/362; 600/584
(58) Field of Search ................................ 600/309, 362, 600/573, 584; 604/361–362, 358; 424/414

(56) References Cited

U.S. PATENT DOCUMENTS

| | | | |
|---|---|---|---|
| 2,981,606 A | | 4/1961 | Keston |
| 3,585,001 A | | 6/1971 | Mast |
| 4,158,546 A | | 6/1979 | Lam et al. |
| 4,231,370 A | | 11/1980 | Mroz et al. |
| 4,327,731 A | | 5/1982 | Powell |
| 5,077,222 A | | 12/1991 | Lau |
| 5,468,236 A | * | 11/1995 | Everhart et al. ............ 604/361 |
| 5,939,088 A | * | 8/1999 | Ito et al. ..................... 424/414 |
| 6,203,496 B1 | * | 3/2001 | Gael et al. .................. 600/362 |

FOREIGN PATENT DOCUMENTS

| | | |
|---|---|---|
| DE | 2604586 | 8/1977 |
| EP | 0444263 | 9/1991 |

OTHER PUBLICATIONS

Patent Abstracts of Japan, No. 04218769 1 page.Shikibe Kazuo Japan Vilene Co. Ltd.

The Merck Index, p. 1480 12 Edition, 1992 1 page Merck Research Laboratories Division.

* cited by examiner

*Primary Examiner*—Robert L. Nasser
(74) *Attorney, Agent, or Firm*—Bierman, Muserlian and Lucas

(57) ABSTRACT

A diaper having indicators incorporated therein for pH, nitrates, bilirubin, ketones, proteins, blood, and urobilinogen. The diaper allows a simple visual examination to obtain information related to the status of the urine emitted by the user, enabling rapid and continuous monitoring of urine status. As a result, appropriate treatment may be directed in a simple, reliable manner.

2 Claims, No Drawings

DIAPER WITH INDICATORS SENSITIVE TO THE STATUS OF THE IMPREGNATED URINE AND VISIBLE FORM OUTSIDE

This application is a 371 of PCT/ES99/00291 filed Sep. 6, 1999.

SUMMARY OF THE INVENTION

The present invention relates to the development of a diaper which incorporates indicators of pH and detectors of other organic substances.

STATE OF THE ART

There are diapers which include precise absorbing substances with the aim of collecting urine and thus avoid any leakage and the effect of wetting the skin of the individual using it. The diaper also prevents the emission of solids. In order to satisfy these needs, there are substances with better absorbing capacity and designs that adjust better to the anatomy of the individual, but none of these diapers is capable of indicating the status of the urine.

THE INVENTION

The present invention incorporates the novelty of improving the role of a conventional diaper to incorporate indicators of determining substances of the status of the urine, how are the pH, the nitrates, the bilirubin, the ketones, the proteins. These indicators consist of supports constituted of a piece of cardboard or other material impregnated with reactive substances that react if they are present in the urine, showing a distinct coloration if the said substances are absent.

Among the advantages that it presents compared to the conventional diapers, on one side, it is possible to detect the acid of the urine and on the other side, the presence or absence of nitrates and brings a very useful orientation and a precocious respect to the status of the urine. It allows also to obtain a continuous information and to follow the evolution. The cost relating to the addition of these indicators to the diapers are very minimal considering the advantages that are provided.

An unlimited example describing the invention:

In the context of the present example, it is understood as a support or indicator a piece of cardboard or other material impregnated with reactive substances that react if they are present in the urine, the said susbtances already mentioned, showing a distinct coloration when they are absent. Here is a better detail of what the indicators describe:

1. Inside the diaper is incorporated a support sensitive to the uric acid, like an absorbent paper or other that shows different colors according to the pH in the urine that wets it.
2. Inside the diaper is incorporated a support that includes para-arsanilic acid and 1,2,3,4-tetrahydrobenzoquinolin (h) 3-ol that react with nitrates modifying visibly its coloration and thus, allows the detection of nitrates in the urine that wets the diaper.
3. Inside the diaper is incorporated a support that includes a diazo 2,4-dichloroaniline salt that reacts with the bilirubin modifying visibly its coloration, and thus, allows detection of bilirubin, if present, in the urine that wets the diaper.
4. Inside the diaper is incorporated a support that includes sodium nitroprussate that reacts with ketones, modifying visibly the coloration and thus, allows detection of ketones in the urine that wets the diaper.
5. Inside the diaper is incorporated a support that includes diisopropylbenzene dihydroperoxide, 3,3',5,5'-tetrametylbenzene that react with the hemoglobin of the blood modifying visibly its coloration, and thus, allows detection of blood in the urine that wets the diaper.
6. Inside the diaper is incorporated a support that includes tetrabromophenol blue that changes with the presence of proteins, changing visibly its coloration and thus, allows detection of proteins in the urine that wets the diaper.
7. Inside the diaper is incorporated a support that includes para-dietylaminobenzaldehyde that reacts with the urobilingena changing visibly its coloration and thus, allows detection of urobilingena in the urine that wets the diaper.
8. Inside the diaper is incorporated a support that includes the glucose oxide and peroxide enzymes and potassium iodide that react with the glucose, changing visibly its coloration and thus, allows detection of glucose in the urine that wets the diaper.
9. The indicators are placed in a way to be in contact with the urine but being at the same time, clearly visible from the outside of the diaper.

In this form, the visibility of the color of the indicators allows detection of the various components that were already described and conclude on the status of the urine that wets them.

The nature of the invention being sufficiently described, and also the realization of its practice in an unlimited example, must be constant so that the previously indicated dispositions are capable of modifications of the details as long as they do not change its fundamental principle.

What is claimed is:

1. A diaper having incorporated therein a support containing a) p-arsanilic acid and 1,2,3,4,-tetrahydrobenzoquindin (h)-3-ol for detection of nitrates, b) a diazo-2,4-dichloroaniline salt for detection of bilirubin, c) sodium nitroprussate for detection of ketones, d) diisopropylbenzene and 3,3',5,5'-tetramethylbenzene for detection of blood, e) tetrabromophenol blue for detection of proteins, f) p-diethylamino-benzaldehyde for detection of urobilingena and g) glucose oxide and peroxide enzymes and potassium iodide for detection of glucose when wetted by urine and the different coloration are visible from the exterior of the diapers.

2. A diaper of claim 1, containing an indicator constituted of organic colorants and which presents a differentiating coloration according to the acid or pH of the urine.

* * * * *